United States Patent [19]

Cook

[11] Patent Number: 5,040,944
[45] Date of Patent: Aug. 20, 1991

[54] PUMP HAVING IMPELLER ROTATIONAL ABOUT CONVOLUTED STATIONARY MEMBER

[76] Inventor: Einar P. Cook, 301 W. Shaw Ave., Clovis, Calif. 93612

[21] Appl. No.: 405,721

[22] Filed: Sep. 11, 1989

[51] Int. Cl.⁵ .............................................. F04D 3/02
[52] U.S. Cl. ...................................... 415/72; 415/900
[58] Field of Search ............................ 417/423.1, 900; 416/176–177; 415/71–76, 900

[56] References Cited

U.S. PATENT DOCUMENTS

| | | | |
|---|---|---|---|
| 536,925 | 4/1895 | Erb | 415/74 |
| 589,532 | 9/1897 | McCoskey | 415/74 |
| 1,111,722 | 10/1914 | Sheahan | 415/74 |
| 1,273,913 | 7/1918 | Ostenberg | 415/74 |
| 1,378,891 | 5/1921 | Musswitz | 415/74 |
| 1,581,683 | 4/1926 | Nicholls | 415/74 |
| 2,256,659 | 9/1941 | Thrasher | 415/73 |
| 2,633,290 | 3/1953 | Schaefer et al. | 415/73 |
| 2,893,688 | 7/1959 | Shada | 415/74 |
| 3,266,555 | 8/1966 | Thier | 415/73 |
| 3,880,548 | 4/1975 | Kirby, Jr. | 415/73 |
| 4,625,712 | 12/1986 | Wampler | 600/16 |
| 4,704,121 | 11/1987 | Moise | 623/3 |

OTHER PUBLICATIONS

"Medicine", feature from *Time*, 16 May 1987.
Wampler et al., "Transactions of the American Society for Artificial Internal Organs", vol. 34, No. 3, Jul.–Sep. 1988, pp. 450–454.
"Hemopom ®" Johnson & Johnson, 1988, pp. 1–14.

*Primary Examiner*—William E. Kamm
*Attorney, Agent, or Firm*—Worrel & Worrel

[57] ABSTRACT

A pump with a tubular housing having a predetermined inlet and outlet, a convoluted stationary member mounted in the tubular housing and a rod extending in a substantially spiral course received within the housing for rotation about the stationary member to move fluid from the inlet through the housing and from the outlet thereof.

6 Claims, 1 Drawing Sheet

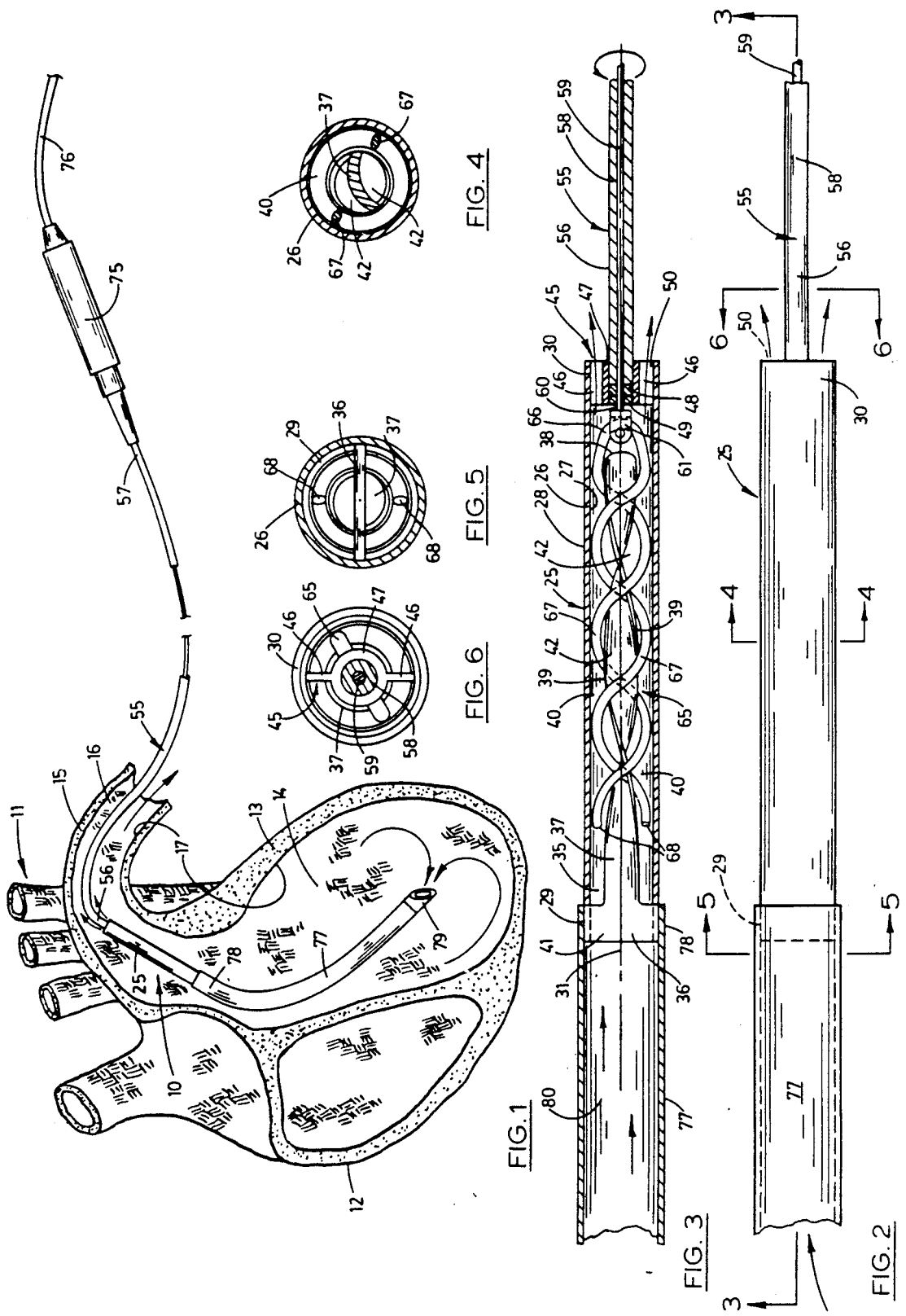

PUMP HAVING IMPELLER ROTATIONAL ABOUT CONVOLUTED STATIONARY MEMBER

BACKGROUND OF THE INVENTION

1. Field of the Invention

The present invention relates to a pump and more particularly to a pump which can be employed in a wide variety of operative environments, but which is particularly well suited to construction in very small sizes operable to assist in the pumping of bodily fluids upon in vivo insertion in a selected fluid passageway such as the aorta of the human heart.

2. Description of the Prior Art

The technologies associated with the pumping of fluids are largely dependent upon the properties of the particular fluid to be pumped and the confines within which the pump must operate. While most pumps must operate within constraints as to size and capacity, there are certain applications in which these constraints are severely limiting. These problems are even more acute where human life may be dependent thereupon.

For example, it has been known to employ miniature blood pumps adapted for insertion into the vascular system of the human body to afford cardiac assistance during a period of trauma and recovery. Thus, it has been known in the event of left ventricular failure following open heart surgery or as the result of a mild cardial infarction to employ such pumps for intraarterial ventricular assist. Such pumps have been maneuvered into the left ventricle of the patient's heart by insertion through an incision in the patient's groin and passage of the pump assembly through the vascular system and into the left ventricle through the aorta. The pump is then driven from a location outside the patient's body by a motor to provide the desired blood flow. This avoids the necessity for a more radical procedure.

While experiments in these areas appear particularly promising, the limitations as to size and capacity of such pumps have interfered with their adoption and usage. Since the assembly is inserted at a site remote from the heart and must be maneuvered along a tortious course, the diameter of the pump itself restricts its use. In order to reduce the outer diameter of the pump to a size capable of such passage, the capacity of such pumps has had to be reduced to a level below that which would be preferred for optimum blood flow. As a consequence, the application of this technology has been limited.

Therefore, it has been known that it would be desirable to have a pump capable of manufacture in extremely small sizes capable of operating at capacities well above that heretofore achieved in pumps of equivalent size and which is particularly well suited to use in the vascular systems of the human body to supplement the flow of bodily fluids during times of trauma and recovery without the need for major surgery or other radical procedures.

SUMMARY OF THE INVENTION

Therefore, it is an object of the present invention to provide an improved pump adaptable for manufacture in a wide variety of sizes and capacities.

Another object is to provide such a pump which is capable of adaptation to a wide variety of operative environments.

Another object is to provide such a pump which can be manufactured in embodiments of extremely small outer diameters with substantially larger capacity than heretofore has been possible.

Another object is to provide such a pump which is of extremely simple and dependable construction capable of operation during long periods at a dependable capacity and with virtually no risk of failure.

Another object is to provide such a pump which produces significantly less trauma to the fluid being pumped then experienced with prior art pumps such as is conventionally associated with the shearing movement between the rotor and the stator in such conventional pumps.

Further objects and advantages are to provide improved elements and arrangements thereof in an apparatus for the purposes described which is dependable, economical, durable and fully effective in accomplishing its intended purposes.

These and other objects are achieved in the pump of the present invention which, in the preferred embodiment, has a tubular housing having a predetermined inlet and outlet, a convoluted stationary member mounted in the tubular housing and an impeller received within the housing for rotation about the stationary member to move fluid from the inlet through the housing and from the outlet thereof.

BRIEF DESCRIPTION OF THE DRAWING

FIG. 1 is a fragmentary schematic diagram showing the pump of the present invention in a typical operative environment in the left ventricle of a human heart which is shown in cross section.

FIG. 2 is a somewhat enlarged, fragmentary side elevation of the pump of the present invention.

FIG. 3 is a longitudinal section taken on line 3—3 in FIG. 2.

FIG. 4 is a transverse section taken on line 4—4 in FIG. 2.

FIG. 5 is a transfer section taken on line 5—5 in FIG. 2.

FIG. 6 is a transverse section taken on line 6—6 in FIG. 2.

DESCRIPTION OF THE PREFERRED EMBODIMENT

Referring more particularly to the drawing, the pump of the present invention is generally indicated by the numeral 10 in FIG. 1.

The pump of the present invention has application to a wide assortment of specific embodiments and uses. More particularly, the pump can be produced in a size, form and from materials suitable for the pumping of virtually any fluid in any operative environment. However, the pump has particular utility when constructed for intraarterial ventricular insertion to provide a temporary cardiac assist. Thus, for illustrative convenience, the pump is shown in FIG. 1 in such a typical operative environment in use in a human heart 11. As shown in FIG. 1, the heart has a right ventricle generally indicated at 12 and a left ventricle generally indicated at 13. The left ventricle encloses a chamber 14. The heart has an aorta 15 which receives blood pumped by the left ventricle. The aorta has a passageway 16. The left ventricle and aorta have interior surfaces 17.

The pump 10 has an elongated tubular housing 25 which may be constructed of any suitable material. However, for use in the embodiment herein disclosed, the housing and all other components of the pump should be constructed of stainless steel. In the embodiment herein disclosed, the housing has an outer diameter of approximately one-quarter of an inch (¼") and a length of approximately one-and-one-quarter inch (1¼"). It will be understood that the actual dimensions and materials from which the pump is manufactured can be varied to suit the particular environment within which the pump is to be employed and as otherwise best suited to the operation to be performed. It will be understood, however, that the pump of the present invention constitutes a significant advancement over the art in that the capacity of the pump is substantially greater than has heretofore been possible for a given outer diameter of the housing 25.

The housing 25 has a cylindrical wall 26 having an interior surface 27 and an exterior surface 28. The cylindrical wall has an inlet end portion 29 and an opposite outlet end portion 30. The cylindrical wall 26 is substantially concentric to a longitudinal axis 31 for the housing 25.

The pump has a core member 35 having a mounting plate 36. The core member is mounted within the cylindrical wall in coaxial relation with the cylindrical wall with the mounting plate 36 mounted on the interior surface 27 of the cylindrical wall at the inlet end portion 29 thereof, as best shown in FIG. 3. The core member includes a convoluted stationary member or fluid vane 37 extending through the housing 25 toward the outlet end portion 30 and wound about the longitudinal axis 31 to form substantially a helix. The fluid vane has a terminal end 38 spaced inwardly of the outlet end portion 30. The fluid vane has marginal edges 39 which are substantially equally spaced from the longitudinal axis 31 to form a passage 40 between the interior surface 27 of the cylindrical wall 26 and the marginal edges. It will be understood that the core member is fixed within the housing so that the fluid vane 37 thereof is similarly fixed relative to the interior surface 27 of the cylindrical wall 26. The inlet end portion 29 has an inlet passage 41 bounded by the cylindrical wall and passing on both sides of the mounting plate 36. The inlet passage communicates both with the passage 40 defined between the marginal edges and the interior surface 27 of the housing 25 and with helical paths 42 defined by the fluid vane 37.

A bearing mounting assembly 45 is itself mounted in the outlet end portion 30 of the housing 25 as best shown in FIGS. 3 and 6. The bearing mounting assembly includes a pair of fluid vanes 46 mounted on the interior surface 27 of the cylindrical wall and extending to and mounting a tubular mount 47 substantially concentric to the longitudinal axis 31 of the cylindrical wall 26. A bearing 48 is mounted within the tubular mount 47 concentric to the longitudinal axis 31. An O-ring 49 is mounted within the tubular mount against the bearing on the side thereof facing the interior of the housing 25. The outlet end portion 30 of the cylindrical wall thus bounds and defines a discharge passage 50 extending outwardly through the outlet end portion about the tubular mount and on both sides of the fluid vanes 46.

A drive cable assembly 55, having a proximal end portion 56 and an opposite distal end portion 57, is mounted by its proximal end portion in the tubular mount 47 of the bearing mounting assembly 45. The drive cable assembly has a stationary outer sheath 58 and an internal rotational drive cable 59. The drive cable has a mounting end 60 which extends through the bearing 48 and O-ring 49 and into the interior of the housing 25 in juxtaposition to the terminal end 38 of the fluid vane 37. A clevis assembly 61 is mounted on the mounting end 60 in coaxial relation to the longitudinal axis 31 and in immediate juxtaposition to the terminal end 38 of the fluid vane 37.

The pump 10 has an impeller 65 best shown in FIG. 3. The impeller has a return bent mounting portion 66 which is mounted on the mounting end 60 of the drive cable 59 by the clevis assembly 61. The impeller includes a pair of impeller rods 67 extending in oppositely wound, spiral courses about the fluid vane 37 of the core member 35 between the marginal edges 39 thereof and the interior surface 27 of the cylindrical wall 26. The impeller rods are thus received within the passage 40 about the fluid vane 37. The impeller rods 67 extend to terminal ends 68 which are spaced from each other substantially 180 degrees about the longitudinal axis 31, as can best be seen in FIGS. 3 and 5. Thus, it will be seen that rotation of the drive cable 59 causes the impeller rods 67 to rotate about the fluid vane 37 in the passage 40 extending thereabout. The impeller can, if desired, also be constructed in the form of a single impeller rod, not shown, extending in a spiral course about the fluid vane.

The distal end portion 57 of the drive cable assembly 55 is connected in driven relation to a suitable high speed electric motor 75 adapted to be driven from a suitable source of electrical energy by way of an electric cable 76 fragmentarily shown in FIG. 1. It will be understood that the drive cable assembly 55 is of a length and of a diameter suitable for extension from the electric motor outside of the body of the patient through the vascular system to the heart 11 as shown in FIG. 1. A semi-flexible inlet cannula 77, having an attachment end portion 78 in an opposite inlet end portion 79, is mounted on the inlet end portion 29 with the attachment end portion 78 slipped outwardly about the inlet end portion 29 of the cylindrical wall 26 of the housing 25 and secured in position by any suitable means. An internal passage 80 interconnects the inlet end portion and attachment end portion thus establishing a path for fluid flow from the inlet end portion 79, along the internal passage 80, through the cylindrical wall 26 of the housing 25 and out the discharge passage 50 of the pump. It will be understood that the inlet cannula 77 is sufficiently flexible to permit it to be wound through the vascular system of the patient, but sufficiently rigid to avoid collapsing.

OPERATION

The operation of the described embodiment of the subject invention is believed to be clearly apparent and is briefly summarized at this point.

As previously described, the pump 10 of the present invention is adaptable for use in a wide variety of operational environments. However, it has particular utility when used in intraarterial ventricular assistance to supplement the pumping of the human heart. Procedures previously developed, such as set forth in the Wampler U.S. Pat. No. 4,625,712, the Moise U.S. Pat. No. 4,704,121 and the article entitled, "IN VIVO EVALUATION OF A PERIPHERAL VASCULAR ACCESS AXIAL FLOW BLOOD PUMP" appearing in Volume XXXIV *Trans Am Soc Artif Intern Organs* 1988, can be employed in using the pump for this purpose. Using these procedures, the pump 10 is maneuvered through the vascular system of the patient to locate the inlet cannula 77, housing 25 and proximal end portion 56 of the drive cable assembly 55 within the chamber 14 of the left ventricle 13 and the passageway 16 of the aorta 15, as shown in FIG. 1.

The electric motor 75 is then operated to rotate the impeller 65 of the housing 25 at the desired number of revolutions per minute. The impeller can be rotated at any desired velocity suited to the requirements of the circumstances. A velocity of up to twenty thousand revolutions per minute (20,000 RPM) may be preferred depending upon the patient's condition. The impeller rods 67 move at high speed about the fluid vane 37 of the core member 35 in the passage 40. The pump operates at significantly higher capacity than conventional pumps to pump blood, within which the pump is submersed, into the inlet end portion 79 of the cannula, through the inlet passage 41, along the passage 40 and the helical paths 42, through the housing 25, out the discharge passage 50 and back into the aorta 15. Such operation supplements the output of the heart thereby relieving the heart muscle from the normal load and permitting the heart muscle to recover and repair itself.

It has been discovered that, for a given outer diameter of the housing 25, the pump has a significantly greater capacity than conventional pumps. Similarly, as can be visualized in FIG. 3, the shearing action between the stator and rotor of conventional pumps is not found in the pump of the present invention thereby reducing significantly the trauma caused to the blood by the pumping operation.

Therefore, the pump of the present invention is adaptable to a wide variety of environments, is capable of being produced in a variety of different sizes best suited to the particular jobs to be performed, operates dependably and safely over a virtually unlimited period of operation to pump fluid therethrough, is particularly well suited to intraarterial ventricular assist to the human heart, significantly reduces the trauma caused to the fluid during the pumping operation and is otherwise substantially more efficient than conventional pumping devices.

Although the invention has been herein shown and described in what is conceived to be the most practical and preferred embodiment, it is recognized that departures may be made therefrom within the scope of the invention which is not to be limited to the illustrative details disclosed.

Having described my invention, what I claim as new and desire to secure by Letters Patent is:

1. A pump comprising a tubular housing having a predetermined inlet and outlet, a convoluted stationary member mounted in the tubular housing, an impeller received within the housing for rotation about the stationary member, and means for interconnecting the impeller and a drive means operable to rotate said impeller about the stationary member to move fluid from the inlet through the housing and from the outlet thereof.

2. The pump of claim 1 wherein said housing is substantially concentric to a longitudinal axis and said stationary member is substantially symmetrical to said longitudinal axis of the housing.

3. The pump of claim 1 wherein said stationary member substantially defines a helix having lateral edges substantially equally spaced from the housing.

4. The pump of claim 3 wherein said impeller includes a pair of rods having a central mounting portion adjacent to the outlet of the housing and extending in a pair of oppositely wound spiral courses toward said inlet end of the housing about said helix of the stationary member.

5. The pump of claim 4 wherein said interconnecting means includes a bearing mounted in substantial alignment with the longitudinal axis of the housing adjacent to the outlet thereof, a drive cable mounted for rotational movement in said bearing, a mount interconnecting the cable and said mounting portion; of the impeller and said drive means for rotating said cable to rotate the pair of rods of the impeller about the stationary member to move said fluid through the housing.

6. The pump of claim 1 wherein said impeller includes an elongated rod extending in a spiral course about the stationary member and said stationary member inwardly of said spiral course of the rod substantially defines a helix.

* * * * *

UNITED STATES PATENT AND TRADEMARK OFFICE
CERTIFICATE OF CORRECTION

PATENT NO.   :   5,040,944
DATED        :   August 20, 1991
INVENTOR(S)  :   Einar P. Cook It is certified that error appears in the above-identified patent and that said Letters Patent is hereby corrected as shown below:

Column 6, Line 33

Delete ";" after the word portion.

Signed and Sealed this

Third Day of November, 1992

*Attest:*

DOUGLAS B. COMER

*Attesting Officer*      *Acting Commissioner of Patents and Trademarks*